United States Patent [19]

Levin

[11] 3,976,601

[45] Aug. 24, 1976

[54] WATER SOLUBLE LUBRICANT FOR TABLETTING COMPOSITIONS

[75] Inventor: Norman A. Levin, Somerville, N.J.

[73] Assignee: Johnson & Johnson, New Brunswick, N.J.

[22] Filed: June 24, 1974

[21] Appl. No.: 482,403

[52] U.S. Cl. ............................ 252/550; 252/89 R; 252/95; 252/99; 252/100; 252/102; 252/103; 252/157; 252/174; 424/16; 424/44

[51] Int. Cl.$^2$............................................. C11D 1/12

[58] Field of Search ............... 252/102, 99, 95, 103, 252/100, 157, 174, 89, 550; 424/44, 16

[56] References Cited
UNITED STATES PATENTS

| | | | |
|---|---|---|---|
| 1,450,865 | 4/1923 | Pelc .................................... | 252/157 |
| 3,116,208 | 12/1963 | Esmund, Sr. ..................... | 252/174 X |
| 3,243,377 | 3/1966 | Stolar et al. ...................... | 252/100 |
| 3,372,125 | 3/1968 | Hill .................................... | 252/157 |
| 3,607,759 | 9/1971 | Barth ................................. | 252/100 |

OTHER PUBLICATIONS

"Carbowax" Polyethylene Glycols, 1–72 pp. 4 and 5, 32.

McCutcheons "Detergents & Emulsifiers, 1971 Annula, "p. 107.

*Primary Examiner*—Mayer Weinblatt
*Attorney, Agent, or Firm*—Steven P. Berman

[57] ABSTRACT

An admixture of spray dried magnesium lauryl sulfate powder and micronized polyethylene glycol polymers has been found to be an excellent lubricant system in tabletting processes for making water-soluble, effervescent tablets such as tabletted denture cleansers, antacids, analgesics and the like. Such lubricant systems are particularly useful when used in the making of an effervescent denture cleanser tablet.

2 Claims, No Drawings

WATER SOLUBLE LUBRICANT FOR TABLETTING COMPOSITIONS

BACKGROUND OF THE INVENTION

This invention relates to lubricating compositions and, more particularly, is directed to water-soluble lubricants useful in tabletting processes for producing water soluble effervescent tablets.

In the making of many effervescent cleansing and medicinal tablets, it is customary to provide the active ingredients in a relatively dry, granular form which are thoroughly blended prior to the tabletting process. The mixed granular ingredients are then fed from a gravity or forced feed hopper into a linear or rotary punch and die press where they are compacted under the influence of pressure into the desired tabletted form. Once the tablet is formed in the die it is released therefrom and suitably packaged for its intended use.

It has also been customary in such tabletting processes to include, along with the granular starting materials, a lubricant in order to permit the granulated starting materials to flow evenly and smoothly through the hoppers of the tablet press and into the die cavities thereof. The lubricants further enhance the compaction of the granulated starting materials into elegant tablets without any sticking or build-up of the granular material on the tablet punches or on the die walls.

Heretofore, the best lubricants for accomplishing such purposes have been insoluble substances such as magnesium stearate or talc. Many water-soluble substances have been tried as lubricants in tabletting processes, substances such as boric acid, sodium benzoate, polyethylene glycol 6000 micronized, boric acid powder, fumaric acid powder, polyvinylpyrrolidone, and the like, but none have been found to function as well in the tabletting process as the insoluble magnesium stearate to talc-like substances.

In the tabletting of active ingredients which desirably are rapidly dissolved in water, such waterinsoluble lubricants which function best in the tabletting process have a deleterious effect on the dissolution of the active ingredients in water. While not only tending to inhibit the rate of dissolution of the water soluble effervescent tablets in water, the insoluble lubricants as have been used heretofore in the tabletting process have also caused the resulting solutions to appear cloudy and unclear.

It would, therefore, be desirable to have a water-soluble lubricant substance or substances which function as well as or better than the water-insoluble lubricants used theretofore, in order to provide tabletted products, such as denture cleansers, antacids, angalgesics and the like, in which the tablet is rapidly dissolved in water to form a sparkling, clear effervescent solution.

SUMMARY OF THE INVENTION

According to the present invention, it has now been found that water-soluble, effervescent tablets can be produced which are rapidly and easily solubilized in water by using in the tabletting process a new water-soluble lubricant composition consisting of an admixture of magnesium lauryl sulfate powder and micronized polyethylene glycol polymer. The tabletting lubricant of the present invention is particularly suitable in formulating rapidly dissolved denture cleanser tablets wherein the evolution of oxygen and carbon dioxide bubbles in water serve as cleansing agents and a sparkling, clear solution results.

DETAILED DESCRIPTION OF THE INVENTION

Water-soluble, effervescent tablets, such as denture cleansers, antacids, analgesics, etc., in general, are made by first thoroughly blending the desired active ingredients along with binders, fillers, extenders, dyes, flavors, etc. in suitable blending apparatus, such as a Hobart mixer, dough kneader, or P-K twin-shell blender and the like. In using the water-soluble magnesium lauryl sulfate powder - micronized polyethylene glycol lubricant of the present invention, it is preferred that the dry granular materials making up the active and filler ingredients be thoroughly blended in a first blending operation and that the water-soluble lubricant admixture be added thereto in a final blending operation, although it is feasible to add the lubricant at any stage of the blending operation.

The magnesium lauryl sulfate portion of the water-soluble lubricant must be in the form of a dry powder having an average particle size ranging from about 12 to about 20 microns and preferably an average particle size of about 16 microns. A particularly suitable magnesium lauryl sulfate is SIPON MLS spray dried powder, available from Alcolac Chemical Company.

The polymeric constituent of the water soluble lubricant system is a polyethylene glycol polymer in micronized form having an average molecular weight ranging from about 6,000 to 20,000. Found to be particularly suitable is CARBOWAX 6,000, available from Union Carbide and which is available in micronized form from Liquid Nitrogen Products Company.

It is preferred that each of the powdered magnesium lauryl sulfate and micronized polyethylene glycol polymer be added to the blended active and filler ingredients in amounts ranging from about 0.05% to about 5% by weight based upon the weight of the total tabletted composition and most preferably in amounts ranging from about 0.2% to about 1% by weight.

For purposes of illustration only, the following specific example of a typical tabletted effervescent denture cleanser is presented which will make even more apparent a typical use of the novel water-soluble lubricant system of the present invention.

EXAMPLE I

To Make 1,000 Denture Cleanser Tablets:

To 15 gms. of polyvinylpyrrolidone dissolved in 100 ml. absolute denatured alcohol, i.e. S.D.A., 3A alcohol, is added 0.015 gm. dimethyl polysiloxane with stirring. This mixture is then slowly added to a Hobart mixer containing 299 gms. citric acid powder U.S.P., 465 gms. tartaric acid powder N.F. and 898 gms. sodium bicarbonate powder U.S.P., all of which are thoroughly blended in the Hobart mixture for 10 minutes. The blended mixture is then dried at 50°C. in a forced draft oven for 18 hours or until the mixture obtains a moisture content of 0.2% or less. The blended and dried mixture is then passed through a 20 mesh sieve and added to a P-K twin-shell blender containing 555 gms. sodium perborate monohydrate, 689 gms. potassium persulfate, 20 gms. sodium lauryl sulfoacetate. The mixture is blended for 15 minutes. 20.25 gms. CARBOWAX 6,000 micronized and 7.6 gms spray dried powdered magnesium lauryl sulfate (16 microns) are added and blending is continued for another 5 minutes.

After thorough blending in the P-K twin-shell blender, the mixture is placed into a feed hopper of a tabletting press. From the hopper, the dry, granular ingredients are measured and fed into the die cavities of the press where the tabletting punches compact the granular material into smooth, shiny surfaced, compact tablets weighing 3.1 gms. each and having a Stokes hardness of 9 to 14 kg.

The finished tablets, when individually dropped into 6 fluid ounces of tap water at 110°F. immediately evolve carbon dioxide bubbles and microbubbles of active oxygen and result in a crystal clear solution. The tablet completely dissolves within 2 minutes.

Because of the free-flowing characteristics of the granular formulation including the powdered magnesium lauryl sulfate - polyethylene glycol polymer lubricant, it is possible to produce in a single die tabletting press up to 90 tablets per minute with no apparent build-up of compacted materials on the die walls or surface of the punches even after the press has been operated for 60,000 cycles.

While the foregoing Example is specific as to ingredients for a single water-soluble denture cleanser tablet, different active ingredients can be used while still incorporating the new magnesium lauryl sulfate-polyethylene glycol polymer lubricant system in the manner described. For example, a denture cleanser tablet formulation can include among others, water-soluble spray dried flavors, and water soluble colors or dyes such as D&C yellow No. 10, technical grade FD&C green No. 1, etc. Similarly, different active oxygen compounds can be incorporated in the denture cleanser tablet; compounds such as sodium carbonate peroxide, potassium peroxydiphosphate, etc. If desired, bleaching compounds that are useful in cleansing dentures and which include active chlorine compounds such as sodium dichloroisocyanurate, sodium hypochlorite, etc. can be used in such water-soluble effervescent tablets.

Furthermore, while the foregoing Example directed to a denture cleanser tablet is specific as to the amounts of the ingredients contained therein, the amounts by weight can be varied over a relatively wide range while still resulting in substantially equivalent cleansing ability. Thus, the ingredients of the denture cleanser tablet can be present in amounts by weight based upon the weight of the tablet as follows:

citric acid powder, from about 8 to about 12 percent; tartaric acid powder, from about 13 to about 17 percent; polyvinylpyrrolidone, from about 0.10 to about 1.0 percent; dimethylpolysiloxane, from about 0.01 to about 0.10 percent; sodium bicarbonate powder, from about 25 to about 35 percent; sodium perborate monohydrate, from about 15 to about 25 percent; potassium persulfate, from about 15 to about 25 percent; sodium lauryl sulfoacetate, from about 0.05 to about 5.0 percent; polyethylene glycol 6000 - micronized, from about 0.05 to about 5.0 percent; and magnesium lauryl sulfate powder, from about 0.05 to about 5.0 percent.

It is also to be understood that the present invention is not limited to water-soluble effervescent denture cleanser tablets, but also is beneficially useful in making water-soluble effercescent tablets containing many varying compounds such as antacids, analgesics and the like.

EXAMPLE II

The following are compositions suitable for preparing water soluble effervescent tablets employing the water-soluble lubricant system of this invention. The tablets may be prepared in a manner similar to that described for the foregoing denture cleanser tablet or in any other conventional or suitable manner.

COMPOSITION I

An antihistamine composition:

|  | Mg/Tablet |
|---|---|
| Citric acid | 145 |
| Tartaric acid | 225 |
| Polyvinylpyrrolidone | 7.5 |
| Dimethyl polysiloxane | 0.75 |
| CARBOWAX 6000 | 10.25 |
| Magnesium lauryl sulfate | 5.13 |
| Sodium bicarbonate | 426 |
| Chlorpheniramine maleate | 2 |

COMPOSITION II

An antihistamine composition similar to that of Composition I except that 8.33 mg of pyrilamine maleate is substituted for chlorpheniramine maleate.

COMPOSITION III

A nasal decongestant composition:

|  | Mg/Tablet |
|---|---|
| Citric acid | 145 |
| Tartaric acid | 225 |
| Polyvinylpyrrolidone | 7.5 |
| Dimethyl polysiloxane | 0.75 |
| CARBOWAX 6000 | 10.25 |
| Magnesium lauryl sulfate | 5.13 |
| Sodium bicarbonate | 426 |
| Phenylephrine hydrochloride | 5 |

COMPOSITION IV

A nasal decongestant composition similar to that of Composition III except that 11 mg of phenylpropanolamine hydrochloride is substituted for phenylephrine hydrochloride.

COMPOSITION V

An antitussive composition in which the components are as described in the nasal decongestant composition (Composition III) except that 10 mg of dextromethorphan hydrobromide is substituted for the phenylephrine hydrochloride.

COMPOSITION VI

A sleeping aid composition in which the components are as described in the nasal decongestant composition (Composition III) except that 25 mg of methapyrilene hydrochloride is substituted for the phenylephrine hydrochloride.

What is claimed is:

1. A water-soluble lubricant admixture for use in tablet compositions consisting essentially of magnesium lauryl sulfate powder having an average particle size of from about 12 to about 20 microns and a micronized polyethylene glycol polymer having an average molecular weight of from about 6,000 to about 20,000.

2. The water-soluble lubricant admixture of claim 1 wherein the magnesium lauryl sulfate powder has an average particle size of about 16 microns and the micronized polyethylene glycol polymer has an average molecular weight of about 6,000.

* * * * *